US00PP08059P

United States Patent [19]

VandenBerg

[11] Patent Number: Plant 8,059

[45] Date of Patent: Dec. 8, 1992

[54] CHRYSANTHEMUM PLANT NAMED WHITE DIAMOND

[75] Inventor: Cornelis P. VandenBerg, Salinas, Calif.

[73] Assignee: Yoder Brothers, Inc., Barberton, Ohio

[21] Appl. No.: 651,003

[22] Filed: Feb. 5, 1991

[51] Int. Cl.[5] ..... A01H 5/00

[52] U.S. Cl. ..... Plt./78

[58] Field of Search ..... Plt./74, 76–81

*Primary Examiner*—James R. Feyrer

*Attorney, Agent, or Firm*—Foley & Lardner

[57] ABSTRACT

A Chrysanthemum plant named White Diamond particularly characterized by its flat capitulum form; decorative capitulum type; white ray floret color with cream center of the flower; diameter across face of capitulum of 133 to 159 mm when fully opened; flowering response period of 49 to 57 days after start of short days; height of 20 to 28 cm when grown as a pinched pot mum with 15 to 18 long days prior to start of short days and 1 to 3 applications of 2500 ppm B-9 SP; spreading branching pattern, with 5 to 6 laterals after pinch; and recommended as disbud pot mum.

3 Drawing Sheets

The present invention comprises a new and distinct cultivar of Chrysanthemum, botanically known as *Dendranthema grandiflora,* and referred to by the cultivar name White Diamond.

White Diamond, identified as 6930 (85-789D02), is a product of a mutation induction program. The new cultivar was discovered and selected by Cornelis P. VandenBerg on Feb. 8, 1988 in a controlled environment in Salinas, Calif., as one flowering plant within a flowering block established as rooted cuttings from stock plants which had been exposed as unrooted cuttings to an X-ray source of 2000 rads in Fort Myers, Fla., on Jun. 18, 1987. The irradiated parent cultivar was an unnamed seedling, identified as 4149 (85-789002), a proprietary breeding line not available in commerce or to other growers. The parent cultivar is a flat decorative disbud pot mum with a very light pink ray floret color, and having a flowering response period of 54 to 62 days after start of short days, a plant height of 23 to 30 cm with one application of 2500 ppm B-9 SP, a spreading branching habit with 5 to 6 laterals after pinch, and a diameter of capitulum of 127 to 155 mm when fully opened. This parent cultivar was discovered and selected as one flowering plant in August of 1985 by Cornelis P. VandenBerg in the progeny of a cross made in 1984. The female parent was the cultivar identified as Charm, a commercially available pink flat decorative disbud pot mum, disclosed in U.S. Plant Pat. No. 5,502. The male parent was an unnamed seedling, identified as 0668 (82-051014) and described as a yellow flat daisy disbud pot mum with many ray florets. Seedling 0668 likewise is a proprietary breeding line not publicly available.

The irradiation program resulting in White Diamond had as its primary objective the expansion of color ranges of the unnamed parent cultivar. The parent cultivar had a very light pink ray floret color, which color was regarded as not commercially acceptable. Because all other traits of the parent cultivar were outstanding, an attempt was made to obtain different ray floret colors, while maintaining all other traits of the parent cultivar.

The irradiation program comprised irradiating cuttings of the parent cultivar 4149 (85-789002) at irradiation levels of 1500, 1750 and 2000 rads. A total of 1264 cuttings harvested from a total of 225 irradiated plants were planted on Nov. 9 and Nov. 30, 1987. Of these, 24 initial selections were made, which selections were then revegetated and reflowered. Four consecutive flowerings resulted in discarding 19 of the original 24 selections on Nov. 9, 1988. Four selections were retained, and one selection was reselected, as possible introductions, to be further tested in our Salinas, Calif. and in our Leamington, Ontario, Canada flowering programs. These flowerings resulted in discarding two out of the five selections on Apr. 26, 1990 and on Jul. 10, 1990, and the decision to commercially introduce one remaining selection as White Diamond. The two other selections, both with yellow ray floret color with bronze overtones, were maintained for further irradiation to obtain a clear yellow ray floret color, without the bronze overtones.

The first act of asexual reproduction of White Diamond was accomplished when vegetative cuttings were taken from the initial selection in April of 1988 in a controlled environment in Salinas, Calif., by technicians working under supervision of Cornelis P. VandenBerg.

Horticultural examination of controlled flowerings of successive plantings has shown that the unique combination of characteristics as herein disclosed for White Diamond are firmly fixed and are retained through successive generations of asexual reproduction.

White Diamond has not been observed under all possible environmental conditions. The phenotype may vary significantly with variations in enviornment such as temperature, light intensity and daylength.

The following observations, measurements and comparisons describe plants grown in Salinas, Calif. under greenhouse conditions which approximate those generally used in commercial greenhouse practice.

The following traits have been repeatedly observed and are determined to be basic characteristics of White Diamond, which, in combination, distinguish this Chrysanthemum as a new and distinct cultivar:

1. Flat capitulum form.
2. Decorative capitulum type.
3. White ray floret color with a cream center of the flower.

4. Diameter across face of capitulum of 133 to 159 mm when fully opened, when grown as a pinched disbudded pot mum.
5. Photoperiodic flowering responds to short days of 49 to 57 days.
6. Plant height, with 15 to 18 long days after sticking unrooted cuttings, and with 1 to 3 applications of 2500 ppm B-9 SP, ranges from 20 to 28 cm when grown as a pinched pot mum with 4 cuttings in a 15 cm pot.
7. Branching pattern is spreading, each plant having 5 to 6 laterals after pinch.
8. Recommended as a disbud pot mum.

The accompanying photographic drawings show typical inflorescence and leaf characteristics of White Diamond, with the colors being as nearly true as possible with illustrations of this type.

Sheet 1 is a color photograph of White Diamond grown as a pinched disbudded pot mum with 4 cuttings in a 15 cm pot.

Sheet 2 is a black and white photograph of three views of the inflorescence of White Diamond.

Sheet 3 is a black and white photograph showing the upper and underside of the leaves of White Diamond at 3 stages of development (mature, intermediate and immature). Sheet 2 includes a measuring tape in centimeters, with the flowers illustrated being smaller than their actual size. The leaves shown in sheet 3 are essentially actual size.

Of the commercial cultivars known to the inventor, the most similar in comparison to White Diamond is the cultivar identified as Envy, a flat white decoative disbud pot mum, disclosed in U.S. Plant Pat. No. 5,986. Reference is made to attached Chart A, which compares certain characteristics of White Diamond with the same characteristics of Envy. Similar traits are capitulum form and type, and ray floret color. White Diamond has a larger diameter of capitulum, a slightly slower flowering response to short days by 1 to 3 days, and more lateral after pinch when compared to Envy.

In the following description color references are made to The Royal Horticultural Society Colour Chart. The color values were determined on plant material grown as a pinched spray pot mum in Salinas, Calif. on Jun. 11, 1990.

Classification:

*Botanical.*—*Dendranthema grandiflora* cv White Diamond.

*Commercial.*—Flat decorative disbud pot mum.

INFLORESCENCE

A. Capitulum:

*Form.*—Flat.

*Type.*—Decorative.

*Diameter across face.*—133 to 159 mm when fully opened.

B. Corolla of ray florets:

*Color (general tonality from a distance of three meters).*—White with cream center.

*Color (upper surface).*—155A with center of flower 4D.

*Color (under surface).*—155A.

*Shape.*—Straight, cross section concave.

C. Corolla of disc florets:

*Color (mature).*—13B to 14B.

*Color (immature).*—144B to 144C.

D. Reproductive organs:

*Androecium.*—Present on disc florets only; very few disc florets, no pollen.

*Gynoecium.*—Present on both ray and disc florets.

PLANT

A. General appearance:

*Height.*—20 to 28 cm when grown as a pinched pot mum with 15 to 18 long days prior to start of short days, with 1 to 3 applications of 2500 ppm B-9 SP.

*Branching pattern.*—Spreading and prolific, with 5 to 6 laterals after pinch.

B. Foliage:

*Color (upper surface).*—147A.

*Color (under surface).*—147B.

*Shape.*—See photograph.

*Size.*—Fully mature, approximately 8–10 cm in length and 5.5–7 cm at the point of greatest width.

CHART A

COMPARISON OF WHITE DIAMOND AND ENVY

| Characteristic | White Diamond | Envy |
|---|---|---|
| Ray floret color | White with cream center | White with cream center |
| Capitulum form and type | Flat decorative | Flat decorative |
| Diameter across face of capitulum | 133 to 159 mm | 127 to 140 mm |
| Flowering response | 49 to 57 days | 48 to 54 days |
| Branching pattern | Spreading 5 to 6 laterals | Spreading 3 to 4 laterals |

COMPARISONS MADE OF PLANTS GROWN AS PINCHED DISBUDDED POT MUMS IN SALINAS, CALIFORNIA

I claim:

1. A new and distinct Chrysanthemum plant named White Diamond, as described and illustrated.

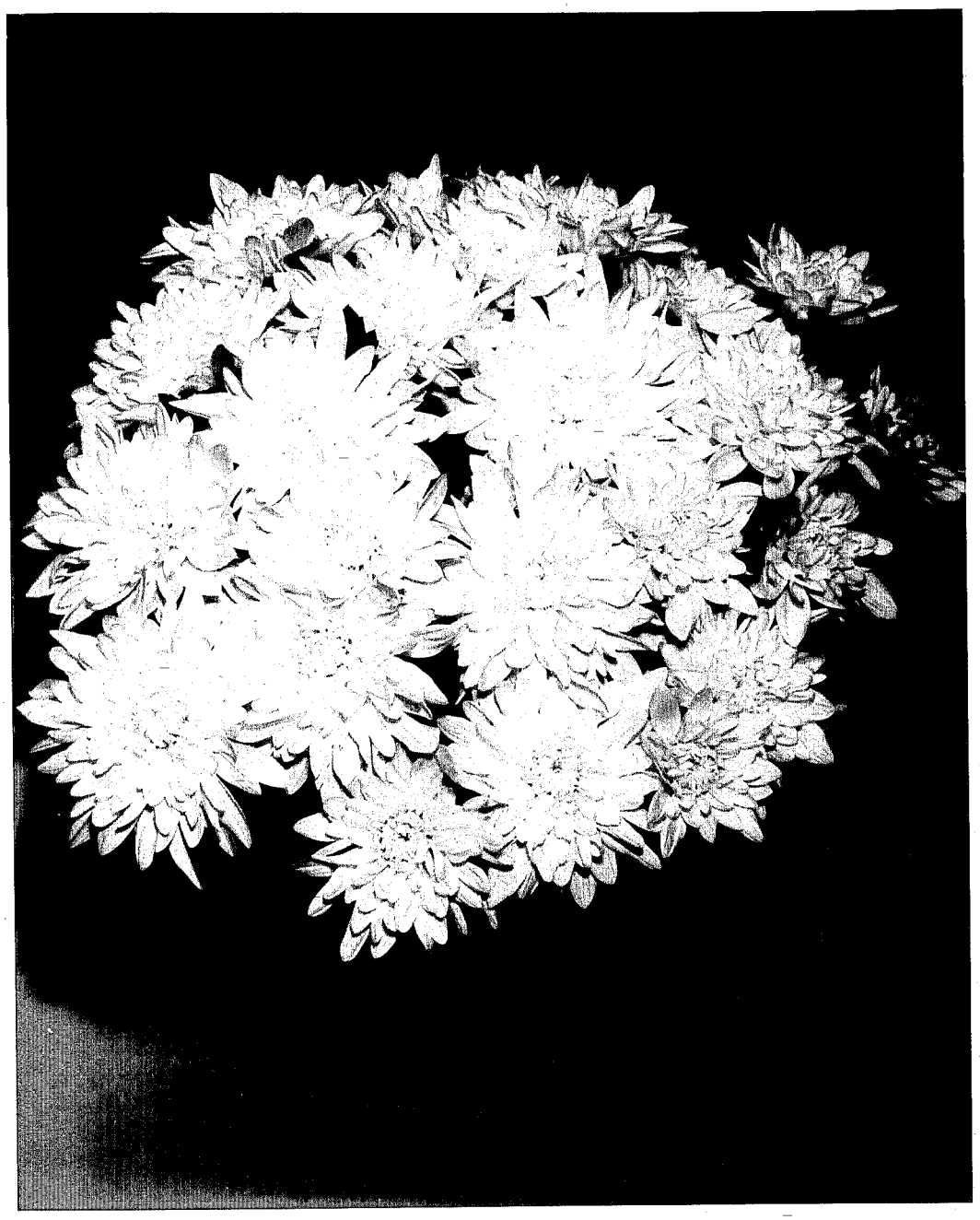

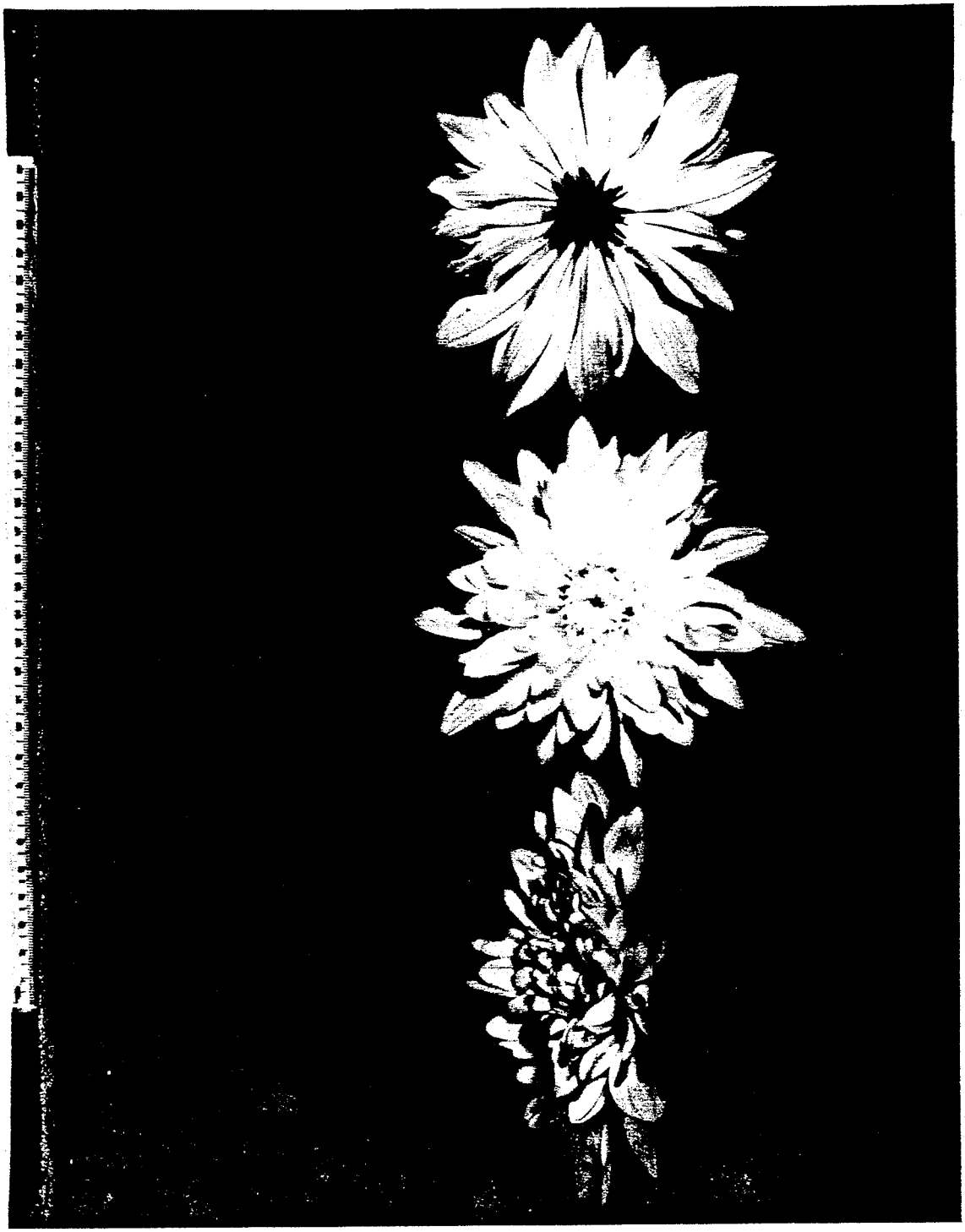

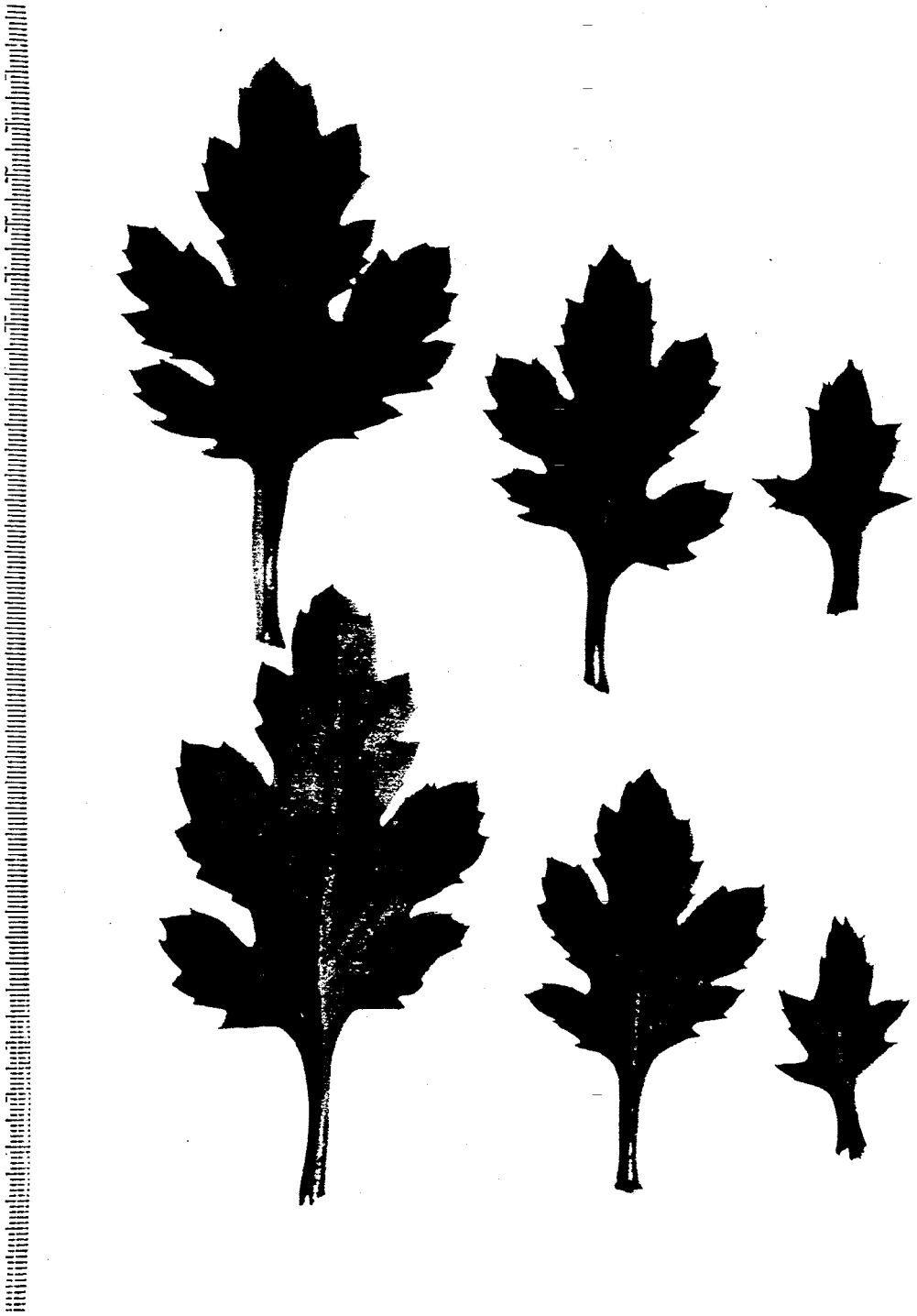

* * * * *